(12) United States Patent
Fletcher et al.

(10) Patent No.: US 7,052,831 B2
(45) Date of Patent: May 30, 2006

(54) DETECTION OF MULTIPLE ANALYTES FROM A SINGLE SAMPLE USING A MULTI-WELL, MULTI-ANALYTE FLOW-THROUGH DIAGNOSTIC TEST DEVICE

(75) Inventors: Robert C. Fletcher, Phoenixville, PA (US); Alvydas J. Ozinskas, Dayton, MD (US); Kenneth Kopher, Baltimore, MD (US); John Gill, Phoenix, MD (US)

(73) Assignee: Becton Dickinson and Company, Franklin Lakes, NJ (US)

(*) Notice: Subject to any disclaimer, the term of this patent is extended or adjusted under 35 U.S.C. 154(b) by 452 days.

(21) Appl. No.: 09/732,838

(22) Filed: Dec. 8, 2000

(65) Prior Publication Data

US 2002/0115062 A1 Aug. 22, 2002

Related U.S. Application Data

(60) Provisional application No. 60/236,153, filed on Sep. 29, 2000.

(51) Int. Cl.
*C12Q 1/70* (2006.01)

(52) U.S. Cl. ............... 435/5; 422/56; 422/57; 422/58; 422/61; 435/7.9; 435/7.92; 435/287.1; 435/287.2; 435/973; 435/975; 436/518; 436/809

(58) Field of Classification Search .......... 422/56, 422/57, 58, 61; 435/287.1, 287.2, 5, 7.9, 435/7.92, 975, 973; 436/518, 809
See application file for complete search history.

(56) References Cited

U.S. PATENT DOCUMENTS

| | | | | |
|---|---|---|---|---|
| 3,770,380 A | * | 11/1973 | Smith | 436/520 |
| 4,299,916 A | * | 11/1981 | Litman et al. | 435/6 |
| 4,366,241 A | * | 12/1982 | Tom et al. | 435/7.91 |
| 4,391,904 A | * | 7/1983 | Litman et al. | 435/7.91 |
| 4,514,508 A | * | 4/1985 | Hirschfeld | 436/518 |
| 4,833,087 A | * | 5/1989 | Hinckley | 422/58 |
| 4,948,442 A | * | 8/1990 | Manns | 156/73.1 |
| 4,948,564 A | * | 8/1990 | Root et al. | 422/101 |
| 5,006,464 A | * | 4/1991 | Chu et al. | 435/7.1 |
| 5,073,340 A | * | 12/1991 | Covington et al. | 422/56 |
| 5,126,276 A | * | 6/1992 | Fish et al. | 436/531 |
| 5,139,934 A | * | 8/1992 | Stewart et al. | 435/7.92 |
| 5,279,935 A | * | 1/1994 | Nycz | 435/5 |
| 5,441,894 A | * | 8/1995 | Coleman et al. | 436/518 |
| 5,494,801 A | * | 2/1996 | Bogart et al. | 435/7.34 |
| 5,571,667 A | * | 11/1996 | Chu et al. | 435/5 |
| 6,063,282 A | * | 5/2000 | Moulton | 210/650 |
| 6,235,464 B1 | * | 5/2001 | Henderson et al. | 435/5 |
| 6,391,541 B1 | * | 5/2002 | Petersen et al. | 435/5 |

OTHER PUBLICATIONS

Ueda et al, "Application of Subtype–Specific Monoclonal Antibodies for Rapid Detection and Identification of Influenza A and B Viruses", Journal of Clinical Microbiology, vol. 36(2), Feb. 1998, pp. 340–344.*

* cited by examiner

*Primary Examiner*—Christopher L. Chin
(74) *Attorney, Agent, or Firm*—S. J. Rittman; M. Lindsey; B. S. Weintraub

(57) ABSTRACT

The present invention provides a method and device for conducting a rapid in vitro enzyme immunoassay test for the direct and qualitative detection of two or more viral antigens from specimens of symptomatic patients. The method for immunoassay of viral antigens is performed on a membrane. Non-immunological capture of viral antigens takes place by absorption onto the membrane. Captured antigen binds to a detection reagent that includes a label conjugated to a specific antibody. The test is a differentiated test such that two or more viral antigens may be distinguished from each other in a single test. The invention also includes a kit for performing an assay in accordance with the method of the present invention, wherein the kit comprises the device of the present invention.

10 Claims, 7 Drawing Sheets

DETECTION OF MULTIPLE ANALYTES FROM A SINGLE SAMPLE USING A MULTI-WELL, MULTI-ANALYTE FLOW-THROUGH DIAGNOSTIC TEST DEVICE

This application claims the benefit of U.S. Provisional Application No. 60/236,153 filed Sep. 29, 2000.

BACKGROUND OF THE INVENTION

Field of the Invention

The present invention relates generally to an assay for detecting and differentiating more than one analyte that may be present in a single patient sample. The present invention at also relates to a device useful for such assays and, more specifically, to an assay device for detecting and differentiating between Influenza A and Influenza B.

DISCUSSION OF THE BACKGROUND

Influenza is an acute viral disease that is seasonal in incidence. The illness classically presents with sudden onset of fever, chills, headache, myalgias and a non-productive cough. Clinical manifestations usually resolve within one week unless complications develop.

The prevalence of influenza varies from year to year. During the past three years, the prevalence of influenza in the United States has ranged between about 28% and about 34%. Influenza A and Influenza B viruses cause the majority of clinically significant diseases, with the Influenza C virus being responsible only for mild, predominantly upper respiratory tract illnesses. The incidence of Influenza B is more sporadic than that of Influenza A. For the 1999–2000 flu season in the United States, about 99.6% of those diagnosed with the flu had Influenza A, compared to only about 0.4% who were diagnosed with Influenza B.

Patients who present with suspected influenza might benefit from treatment with antiviral agents. Amantadine (SYMMETREL®) and rimantadine (FLUMADINE®) are available for the prevention and treatment of Influenza A only. Zanamivir (RELENZA®) and oseltamivir (TAMIFLU®) are available for treatment of both Influenza A and Influenza B. In adults, therapy with any of these agents may reduce the severity and duration of the illness if given within the first 48 hours of the onset of the illness.

A variety of assay systems that are both rapid and sensitive have been developed to detect or determine the concentration of a substance, generally referred to as an analyte, present in a fluid sample. Conventional immunoassays depend on the binding of an antigen or hapten to a specific antibody and have been particularly useful because they give high levels of specificity and sensitivity. These assays generally employ a reagent in labeled form, the labeled reagent often being referred to as the "detection reagent" or the "tracer."

Various means for labeling have been developed and are routinely employed in conventional assay systems. Radioimmunoassay ("RIA") procedures, which use radioisotopes as labels, provide high levels of sensitivity and reproducibility and are amenable to automation for rapid processing of large numbers of samples. Fluoroimmunoassay ("FIA"), which uses fluorochromes as labels, provides direct detection of the label by exciting the dye with excitation radiation of appropriate wavelength and detecting fluorescence therefrom.

Enzymes have often been used as labels in immunoassays. In conventional enzyme innmunoassay ("EIA"), an enzyme is covalently conjugated with one component of a specifically binding antigen-antibody pair, and the resulting enzyme conjugate is reacted with a substrate to produce a signal that is detected and measured. The signal may be a color change, detected with the naked eye or by a spectrophotometric technique, or may be conversion of the substrate to a product detectable by fluorescence.

A convenient format for EIA is solid phase immunoassay in which one of the assay reagents is immobilized on a solid support. The solid support may be in the form of a dipstick, the inside wall of a test tube or cuvette or the well of a microtiter plate. A particularly useful solid phase support is a microporous membrane. Flow-through assay devices in which flow is enhanced by capillary action induced by an absorbent pad in contact with the membrane of the type disclosed in U.S. Pat. No. 4,632,901 to Valkirs are commonly employed.

Numerous assays and devices have been reported in the prior art. Each of these, however, fails to contemplate or address the problems solved by the present invention, as well as the unexpected and surprising results that are achieved by the present invention.

For example, U.S. Pat. Nos. 5,747,274 and 5,710,008, both to Jackowski et al., disclose an assay method and device for assessing whether patient chest pain is cardiac in origin and for differentiating between unstable angina and myocardial infarction as the cause of patient chest pain. The device, however, only has one common site for application of the sample, i.e., it contains a single well. Moreover, after application of the sample, the sample migrates by capillary action and contacts the detector section, followed by the capture section such that it contacts all detector and capture antibodies present in the device.

U.S. Pat. No. 5,208,143 to Henderson et al. discloses a device and method for a solid phase immunoassay for a viral antigen. The device comprises only a single receiving well into which the sample and all other liquids are placed, while the method determines the presence of only a single viral antigen. Because of its design, the device and method of Henderson et al. are not readily adaptable to the detection of more than one antigen.

Khalil et al., in U.S. Pat. No. 5,006,309, discloses a dual-well, immunoassay device. The device is designed to allow for transfer of the sample and the reagent mixture from the first well to the second well via a communicating passage means. The device allows for communication between the wells and, therefore, suffers from the same drawbacks as other prior art devices and methods.

U.S. Pat. No. 4,981,786 to Dafforn et al. discloses a multiple port assay device. While the device comprises more than one well, the sample is introduced into a first well, and a liquid reagent other than the sample is introduced into a second well. Moreover, the sample and liquid reagent migrate long the device by capillary action such that there is communication between the wells. This device, therefore, suffers from the same drawbacks as other prior art devices and methods.

U.S. Pat. No. 4,977,078 to Niimura et al. discloses an immunoassay device that includes a plate substrate having a flat surface, a plurality of adjacent projections projecting on the flat surface and a plurality of immunoreaction regions formed by applying and fixing immunoassay reagents to and in the flat regions defined by the adjacent projections. While this device includes a plurality of immunoassay regions, the immunoassay regions are not constituted by wells.

The prior art assays and devices fail to address the need for a simple, reproducible and accurate means of detecting the presence of and differentiating between two or more analytes in a single patient sample. The prior art devices and methods also fail to provide a means of detecting and differentiating between two closely related samples while at the same time ensuring against cross-reactivity and/or contamination, i.e., such as that which is observed in devices that employ a plurality of wells in communication with each other by capillary or other action.

Additionally, while procedures have been reported for the diagnosis of Influenza A or Influenza B, these are not methods or devices that allow for the rapid detection of and differentiation between Influenza A and Influenza B in a single patient sample. Procedures used to diagnose Influenza A and Influenza B viral infections include rapid immunoassay, direct specimen immunofluorescence assay, reverse transcription-polymerase chain reaction ("RT-PCR"), serologic assay and culture isolation with confirmation. Iminunofluorescence assays entail staining of specimens immobilized on microscope slides using fluorescent-labeled antibodies for observation by fluorescent microscopy. Culture methods employ initial viral isolation in cell culture, followed by hemadsorption inhibition, immunofluorescence or neutralization assays to confirm the presence of the influenza virus.

Because the therapeutic options have expanded to include options for treatment of Influenza B, it would be advantageous to be able to rapidly distinguish between Influenza A and Influenza B to give physicians a choice in selective antiviral intervention. Moreover, because only amantadine and rimantadine have indications for prophylaxis of Influenza A, it would be advantageous to determine if Influenza A was causing symptomatic disease in a particular institution (e.g., a nursing home) or community, so that appropriate preventative measures could be taken with respect to susceptible individuals. It is, therefore, important to not only rapidly determine whether influenza is present, but also which type of influenza virus is present.

In view of the aforementioned deficiencies attendant with the prior art methods, it is clear that a need exists for a rapid immunoassay test that can detect and differentiate between two or more analytes, particularly Influenza A and Influenza B, that may be present in a single patient sample.

SUMMARY OF THE INVENTION

One object of the present invention is to detect and differentiate between two or more analytes that may be present in a single patient sample.

Another object of the invention is to detect and differentiate between Influenza A and Influenza B viral antigens that may both be present in a single patient sample.

To achieve the foregoing and other objects, and in accordance with the purpose of the present invention as embodied and broadly described herein, the present invention relates to a method and device capable of detecting and differentiating, in separate wells, two or more analytes in a single sample. In a preferred embodiment, the present invention is a rapid in vitro enzyme immunoassay membrane test for the direct and qualitative detection of Influenza A and/or Influenza B viral antigens from specimens of symptomatic patients. The test of the present invention is a differentiated test and can, therefore, distinguish Influenza A viral antigens from Influenza B viral antigens in a single test.

In one embodiment, the present invention comprises a dual- or multi-well flow-through diagnostic device comprising a device top having a plurality of non-communicating wells, a device bottom, an absorbent pad between the device top and bottom and a membrane between the device top and the absorbent pad.

In another embodiment, the present invention is a method of detecting and differentiating two or more analytes that may be present in a single patient sample. The membrane is the location of analyte binding and of detection and differentiation. The presence of two or more analytes in a single sample may be differentiated by detection in separate wells using individually distinct detection reagents that bind to the analytes that are captured on the membrane. According to the present invention, the sample, which may or may not be processed, is added to each well. The analyte or analytes present in the sample are captured by the membrane. Detection reagents are added to the wells, followed by addition of a substrate for color development and subsequent visual detection.

The present invention is an improvement over previous flow-through diagnostic test devices. This improvement is accomplished broadly by several underlying technical principles. One such principle is that a single patient sample that may contain more than one analyte is divided among a plurality of non-communicating wells on a single test device such that at least one analyte is captured on the membrane in at least one of the wells by liquid flow of the sample through the membrane. Another is the addition and binding of one or more individually distinct detection reagents in a manner that can differentiate the analytes. The binding of the detection reagents forms detectable regions on the membrane surface.

The above and other objects, advantages and features of the present invention will become more apparent from the following detailed description of the presently preferred embodiments, when considered in conjunction with the drawings, and to the appended claims.

DESCRIPTION OF THE PREFERRED EMBODIMENTS

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. Numerous variations may be made by persons skilled in the art without departure from the spirit of the invention. The scope of the invention will be measured by the appended claims and their equivalents.

Figure 1:
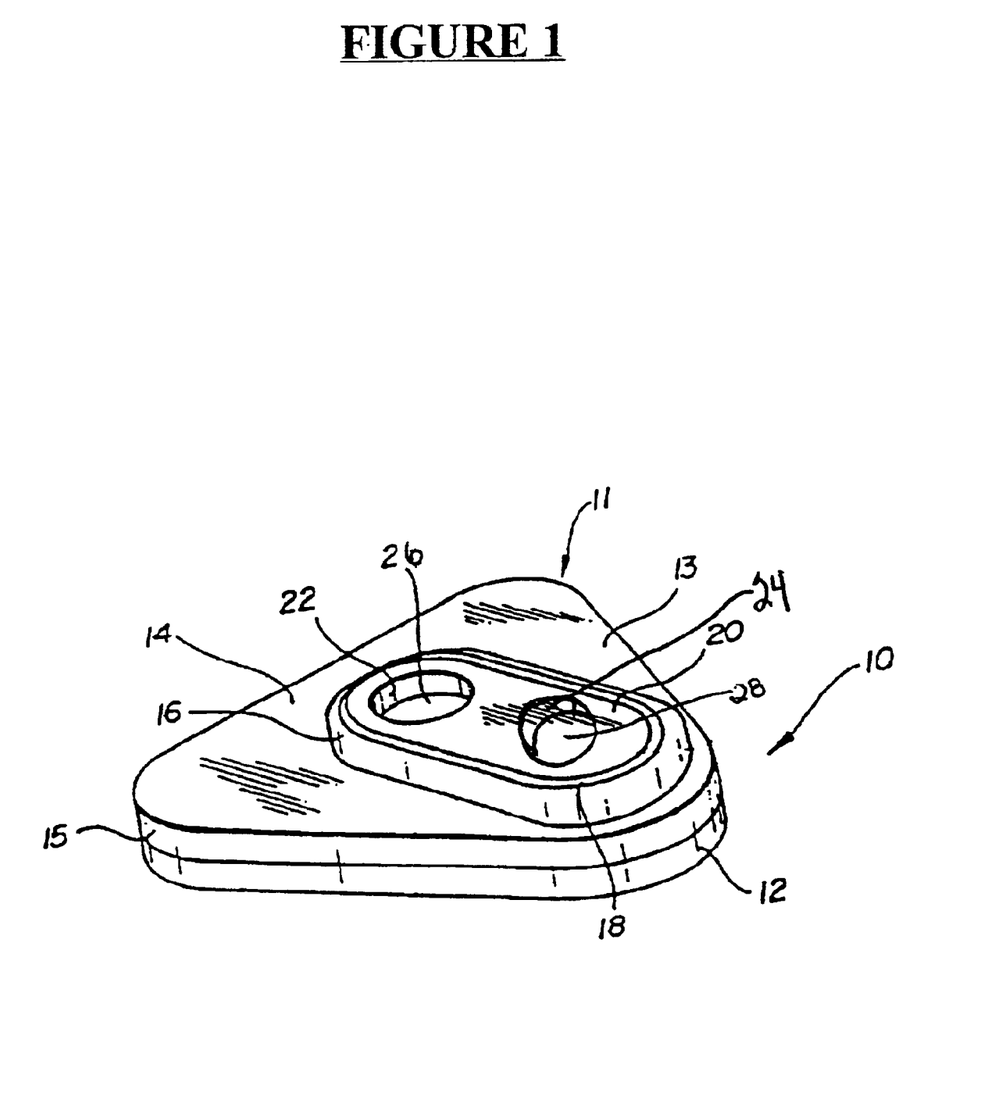
FIG. 1 is a perspective view of the preferred assay device of the present invention.

The assay device of the present invention will first be described by reference to the figures. FIG. 1 illustrates device 10 including an enclosure 11 having a base portion 12 and a lid portion 13. Lid 13 includes a top wall 14 and a substantially vertical side wall 15. A rim 16 projects upwardly from top wall 14. Rim 16 defines a recess 18 having therein an insert 20, which is preferably colored. Insert 20 has at least two openings 22 and 24 in alignment with at least two openings 26 and 28, respectively, in lid 13 to form at least two wells in device 10.

Figure 2:
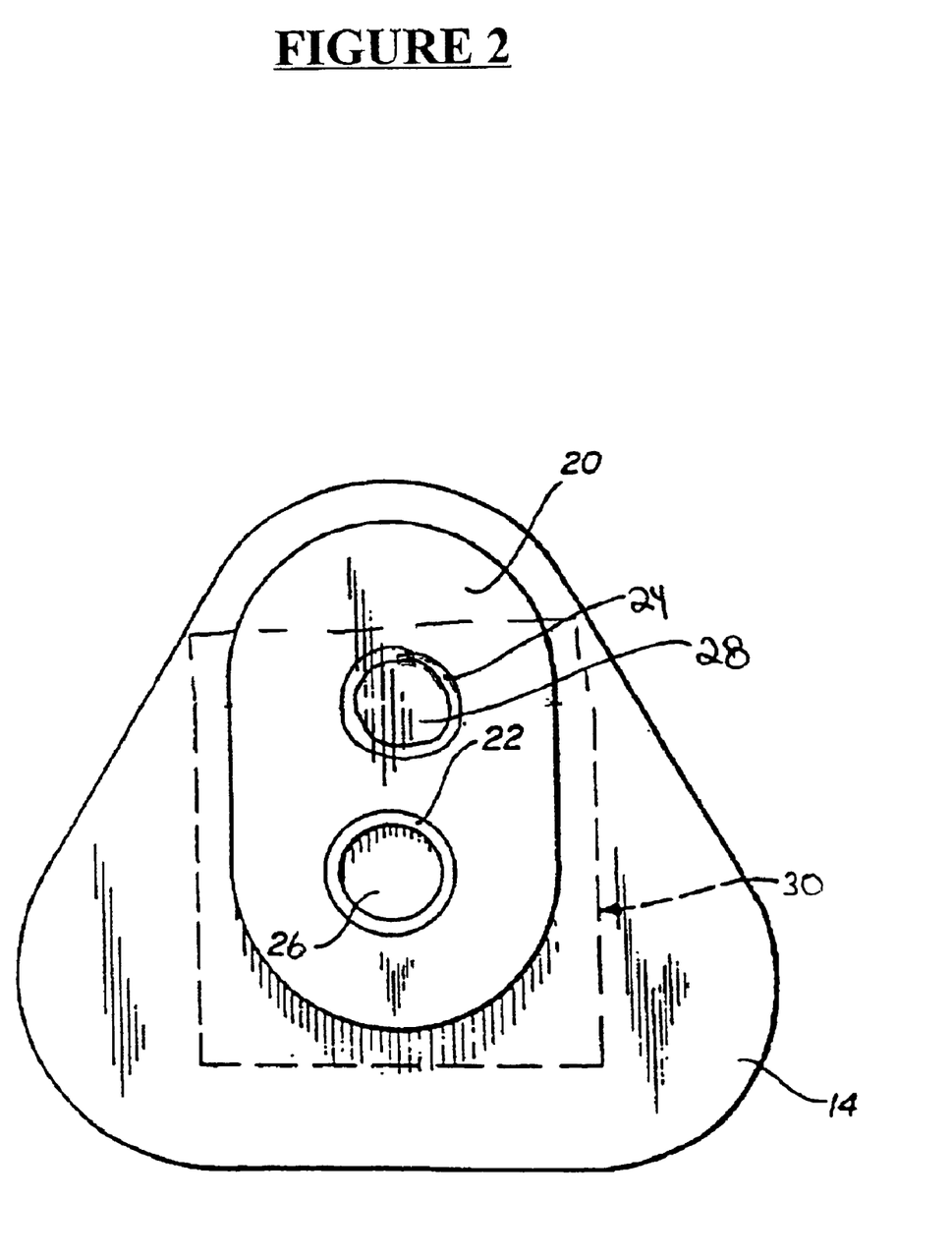
FIG. 2 is a top perspective view of the assay device of the present invention showing the filter stack in phantom.

FIG. 2 shows a filter stack 30 in phantom positioned under openings 22 and 24 and openings 26 and 28.

Figure 3:
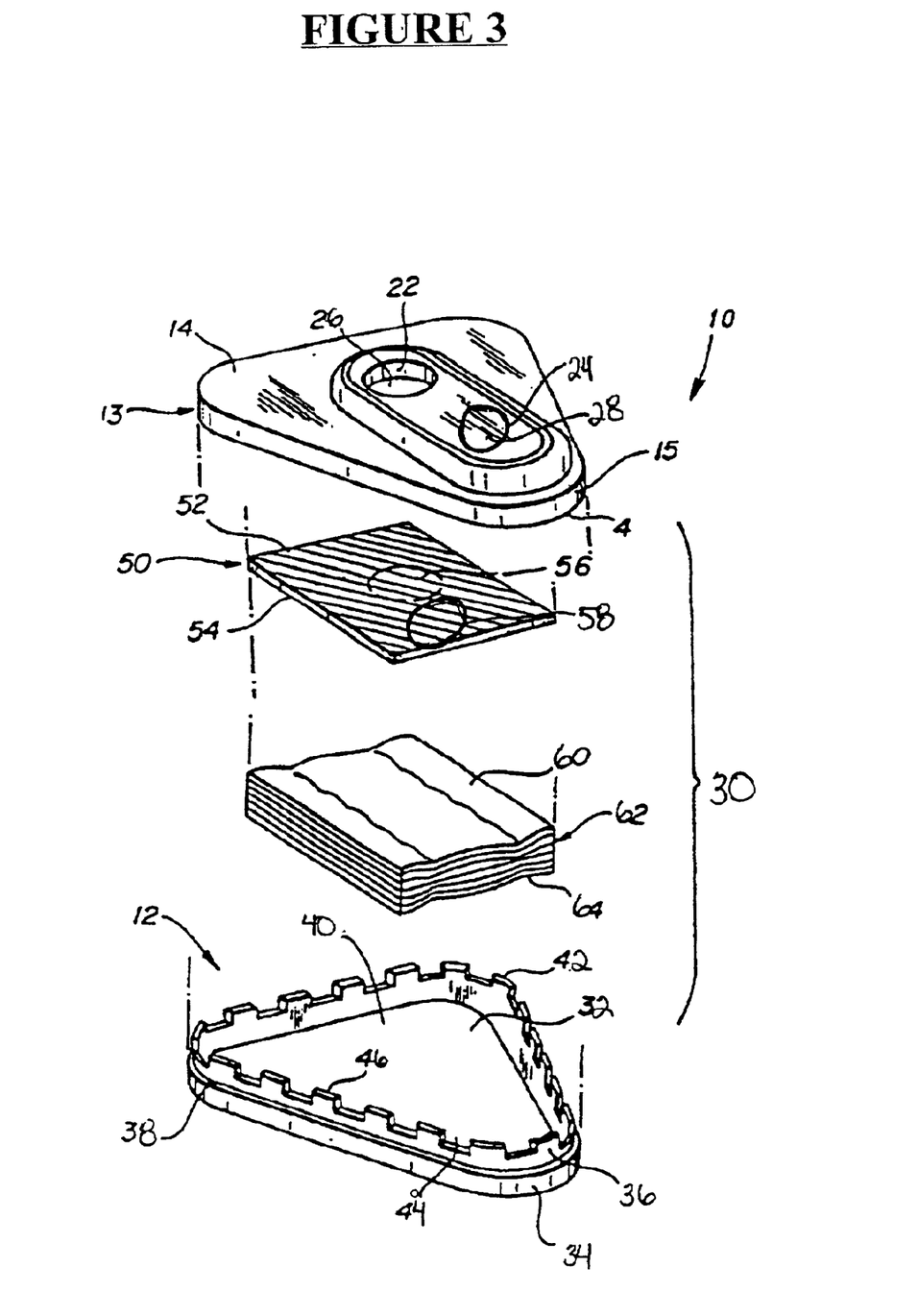
FIG. 3 is an exploded perspective view of the preferred assay device of the present invention showing the arrangement of the components of the device.

Details of base portion 12 and filter stack 30 are more clearly illustrated in FIG. 3. Base portion 12 has a bottom wall 32 and a substantially vertical side wall separated into lower section 34 and upper section 36 by a substantially horizontal shelf 38. Bottom wall 32 and side wall sections 34 and 36 together define a chamber 40 that receives filter stack 30.

Upper section 36 has a plurality of projections 42 extending upwardly therefrom. Projections 42 are separated from each other by spaces 44. When device 10 is assembled as shown in FIG. 1, top wall 14 of lid 13 rests on upper surfaces 46 of projections 42 so that the lower edge 48 of side wall 15 is preferably positioned slightly above horizontal shelf 38, thereby providing air communication from the external environment to chamber 40 through spaces 44.

The device is to be constructed to ensure that there is no communication between the two or more wells of any measure or by any means.

Insert 20, base portion 12 and lid 13 may be made of any plastic material such as polyethylene, polystyrene and polypropylene. Polypropylene is most preferred. Insert 20 may be of any color and is preferably a color that contrasts with the color that develops on test areas 56 and 58 when a positive assay is indicated. It is also understood that device 10 may be of any shape and is not limited to the triangular shape shown in the drawings.

Filter stack 30 includes a porous membrane 50 having an upper surface 52 and a lower surface 54. Upper surface 52 preferably includes test areas 56 and 58. Test areas 56 and 58 are respectively positioned below openings 22 and 24 of insert 20 and openings 26 and 28 of lid 13. Test areas 56 and 58 may be coated with a binder, as described below.

Membrane 50 may be of any material that wets readily with an aqueous assay solution. Membrane 50 preferably is a material suitable for attachment of an assay binding reagent, such as a capture antigen or a capture antibody. Suitable materials for membrane 50 are, for example, glass, nylon and cellulose. Preferred membranes may be made of nylon or nitrocellulose. Particularly preferred membranes are commercially available from Pall Corporation, East Hills, N.Y., under the names IMMUNODYNE® and BIO-DYNE® A, B and C.

Lower surface 54 of membrane 50 is positioned to contact a pad 60 of absorbent material having an upper surface 62 and a lower surface 64. Lower surface 64 of pad 60 rests on bottom wall 32 of base portion 12. While FIG. 3 shows pad 60 to include a plurality of members, it is evident that a single pad of appropriate thickness may be used. Alternatively, the plurality of members may be sewn together or attached by any other convenient means.

Absorbent pad 60 comprises a porous material having an absorbing capacity sufficient to absorb substantially all the liquids of the assay reagents and any wash solutions. Pad 60 also serves to initiate capillary action, which draws the assay liquids through test areas 56 and 58. As such, pad 60 may preferably be formed from a cellulose material such as, for example, absorbent cellulose paper. Suitable absorbent cellulose paper is commercially available from Filtration Sciences, Mount Holly Springs, Pa.

If desired, filter stack 30 may include additional layers (not shown) such as those described in U.S. Pat. No. 5,073,340 to Covington et al. and U.S. Pat. No. 5,185,127 to Vonk, the entirety of each of those patents being incorporated herein by reference.

Figure 4:
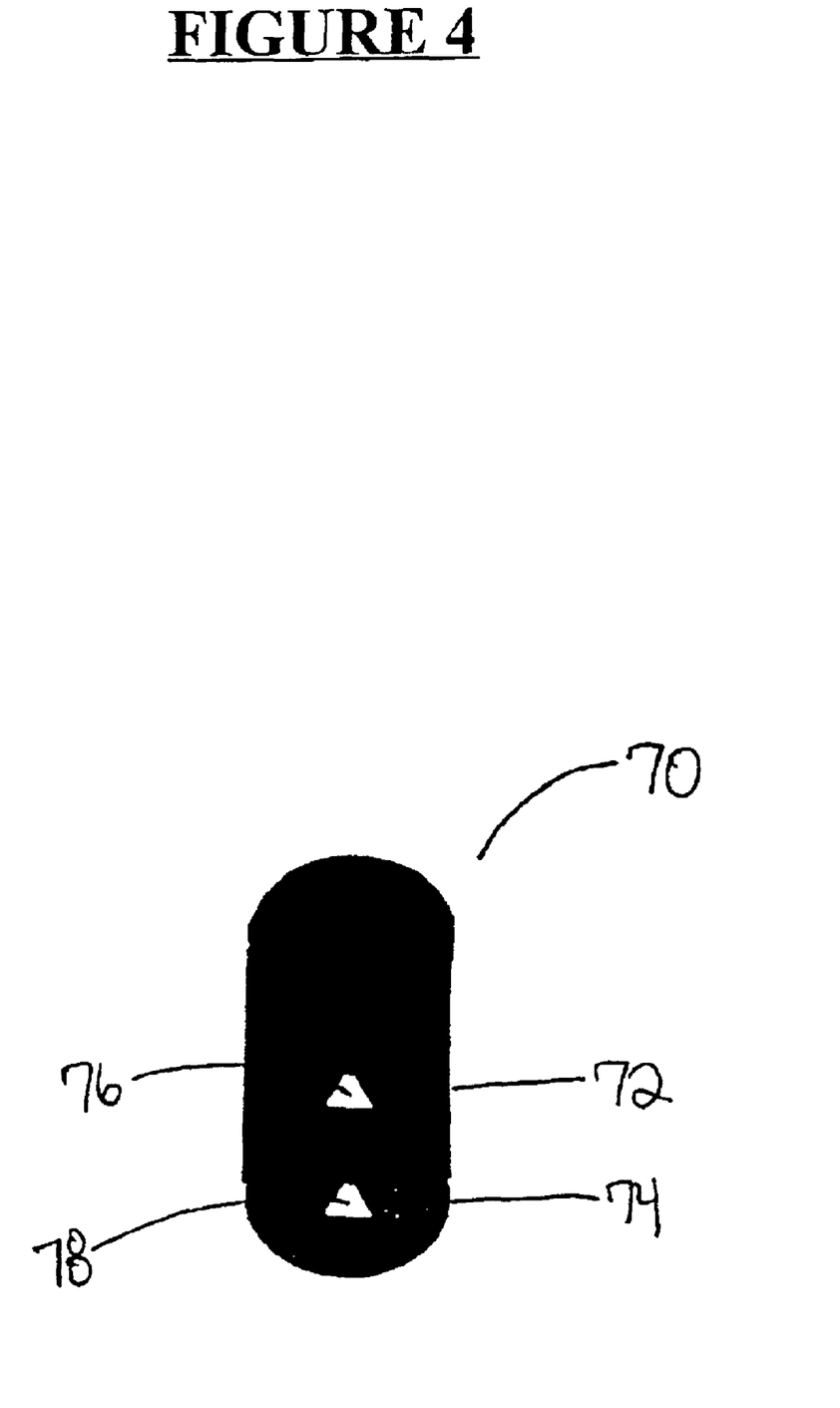
FIG. 4 is a perspective view of a flow controller unit that is part of the present invention.

Referring now to FIG. 4, device 10 preferably includes a flow controller unit 70. Flow controller unit 70 is a molded, preferably plastic, insert having at least two wells 72 and 74. The number of wells in the flow controller unit is equal to the number of wells in the device such that each well of the flow controller unit fits into one of the wells of the device, i.e., wells 72 and 74 fit into the wells in device 10 formed by openings 22 and 24 of insert 20 and openings 26 and 28 of lid 13. The bottom of each well 72 and 74 has an opening 76 and 78, respectively, in the shape of, for example, a triangle. It is understood that while the shape of each of openings 76 and 78 is described herein as a triangle, any shape is acceptable so long as openings 76 and 78 are smaller than wells 72 and 74 so as to control the flow of the sample through test areas 56 and 58. Openings 76 and 78 touch upper surface 52 of membrane 50 when flow controller unit 70 is inserted into device 10.

Device 10 may further include both internal positive and negative procedural controls. Preferably, on the membrane located in the center of one of the wells (hereinafter referred to as the "A well" or "upper well") is a control dot of recombinant Influenza A (H1N1) antigens. Similarly, preferably located on the membrane in the center of the other well (hereinafter the "B well" or "lower well") is a control dot of recombinant Influenza B (Lee 40) antigens. The appearance of the small control dot in the center of the wells during the test provides an internal positive procedural control that both validates the immunological integrity of the device and proper reagent function and assures that the correct test procedure has been followed. The membrane area surrounding both the control dot and the area indicating a positive reaction (as will be later described in detail) is the internal negative procedural control for the test device. The lack of significant color development in this background area to obscure the indication of a positive reaction or the control dot indicates that the test has been performed correctly.

As mentioned above, the membrane may be coated with a binder for an analyte. If the analyte is an antigen, then the binder to be coated on the membrane is generally a specific antibody, often referred to as a "capture antibody." If the analyte is an antibody, then the binder may be a specific antigen, referred to as a "capture antigen." Binder, however, is not required if the analyte is an Influenza A and/or Influenza B viral antigen. In such instances where the analyte is an Influenza A and/or Influenza B viral antigen, the antigen non-specifically binds to the membrane in the absence of binder as described in U.S. Pat. No. 5,208,143 to Henderson et al., the entirety of which is incorporated herein by reference.

In a preferred embodiment, the test device of the present invention employs an enzyme immunomembrane filter assay to detect Influenza A and/or Influenza B antigens extracted from suitable specimens of symptomatic patients. Suitable specimens include, but are not limited to, nasopharyngeal wash, nasopharyngeal aspirate, nasopharyngeal swab, lower nasal swab, throat swab and bronchoalveolar lavage.

Broadly, according to the method of the present invention, the membrane in each of the A well and the B well is exposed to the specimen suspected of containing one or more viral antigens. Preferably, the membrane in the wells is incubated with the specimen in a flow-through format for about 1 to 15, preferably less than 5, minutes at a temperature of about 15° to about 30° C., preferably at or around ambient temperature. By this procedure, one or more antigens present in the specimen binds to the membrane in the wells. Antigenic drift is not an issue with the test of the present invention because the target antigens are the nucleoproteins, which are type-specific and are highly conserved.

In accordance with the present invention, the membrane in each well having one or more viral antigens captured thereon, as described above, is incubated with a detection reagent. More particularly, into each of the detection wells is added an individually distinct detection reagent. The detection reagent placed in each well preferably comprises an antibody specific for the antigen having a label conjugated thereto. The label may be any conventional marker that, after the binding of the detection agent to the one or more antigens captured on the membrane, gives rise to a signal that may be detected. Accordingly, the label may be a radioactive atom or fluorescent dye conjugated to the antibody. When the label is a radioactive element, the signal is radioactive counts. A typical radiolabel is, for example, $^{127}$I. When the label is a fluorescent dye, the signal is fluorescent emission detected after application to the dye of excitation light of suitable wavelength. A typical fluorescer is, for example, fluorescein isothiocyanate ("FITC"). Conjugation of radioactive and fluorescent labels to antibodies is conventional, and no further details on preparation and use of radiolabels and fluorescent labels in immunoassay are needed for a complete understanding of the invention by one skilled in the art.

Preferably, the present invention utilizes enzyme conjugates as the detection method. Suitable enzyme conjugates that may be used for detection include, for example, antibody-enzyme conjugates and enzyme-ligand conjugates. Most preferably, detection is by means of antibody-enzyme conjugates. Any enzyme that may be conjugated to the antibody and for which a substrate convertible to a colored product exists may be used. Suitable enzymes are, for example, cyclases, isomerases, peroxidases and hydrolases such as peptidases, esterases, phosphatases and glycosidases. Conjugation of enzymes to antibodies is well-known and fully understood by those skilled in the art. In a variation of the present invention, other ligand conjugates such as, for example, particle-ligand conjugates including but not limited to colloidal metals (i.e., gold), latex (i.e., microspheres of polystyrene) and liposomes, fluorophore-ligand conjugates and other detector-ligand conjugates may also be used.

In accordance with the present invention, individually distinct detection reagents are added to each of the wells having viral antigen captured in the membranes thereof to induce immunological binding of the antigen and antibody component to the membrane. Subsequently, the membrane having a bound antigen-antibody fraction thereon may then be separated from the liquid phase of the assay medium by any suitable method, preferably by causing the liquid to pass through the membrane. Liquid flow through the membrane may be by gravity or, preferably, may be enhanced by capillary action induced by the absorbent material positioned under the membrane. The membrane may then be treated with wash solutions in accordance with conventional immunoassay procedures. The membrane may subsequently be treated with a liquid such as water, saline or buffer in which an enzyme substrate is dissolved. Enzyme in the bound fraction converts the substrate to a product detectable by a signal associated with color. The signal detected may be the development or disappearance of a color or a change from one color to another. It is preferred that the substrate be colorless until cleaved by the enzyme label to give a colored product. If desired, a reagent to stop further color development may be added. Addition of such reagent provides a time during which results may be interpreted.

The method of the present invention will now be described with specific reference to Influenza A and Influenza B; however, it is understood that while the presently preferred method encompasses detection and differentiation of Influenza A and Influenza B, the method of the present invention is not so limited.

In this preferred embodiment, a suitable respiratory specimen is obtained from a symptomatic individual suspected of having Influenza A and/or Influenza B. Influenza A and/or B viral antigens may be extracted from the specimen by mixing the specimen with an appropriate extraction reagent. A sample of the extracted specimen is then dispensed into each of the wells of the test device. The extracted specimen is preferably dispensed into the wells dropwise, alternating single drops between the A and B test wells until 4 drops have been added to each well of the test device. Preferably, the specimen is expelled into the wells through a filter assembly to remove particulates and solid materials, thereby allowing the specimen to absorb completely.

As the specimen passes through the flow controller, Influenza A and/or B antigens present in the specimen non-specifically bind to the membrane surface in the A and B wells. Preferably, the antigens present in the specimen bind to the membrane in the shape of a triangle. While a triangular shape is preferred, it is understood that the pattern may be any shape and is not limited to any given shape.

Antigen captured on the membrane may be detected after washing the membrane with a suitable wash reagent. Subsequently, a detection reagent containing enzyme-conjugated monoclonal antibodies (2) specific for Influenza A nucleoprotein antigen is added to the upper, or A, well of the test device. A detection reagent containing enzyme-conjugated monoclonal antibody specific for Influenza B nucleoprotein antigen is added to the lower, or B, well of the test device. The enzyme-antibody conjugates bind to trapped antigen following their addition to the membrane in each of the wells.

The captured influenza antigen-antibody complex may be visually detected by an enzymatic color development in the shape of, for example, a purple triangle. It is to be understood that the color is not limited to purple and that the shape is not limited to a triangle. Enzymatic color development in the shape of a purple triangle on the membrane in either the upper well or the lower well of the test device indicates a positive test for Influenza A or for Influenza B, respectively. Similarly, such color development in both wells indicates a positive test for both Influenza A and Influenza B. The absence of enzymatic color development in the shape of a purple triangle and the formation of a small control dot only indicates a negative test. The total test time is less than about 15 minutes.

Figure 5:
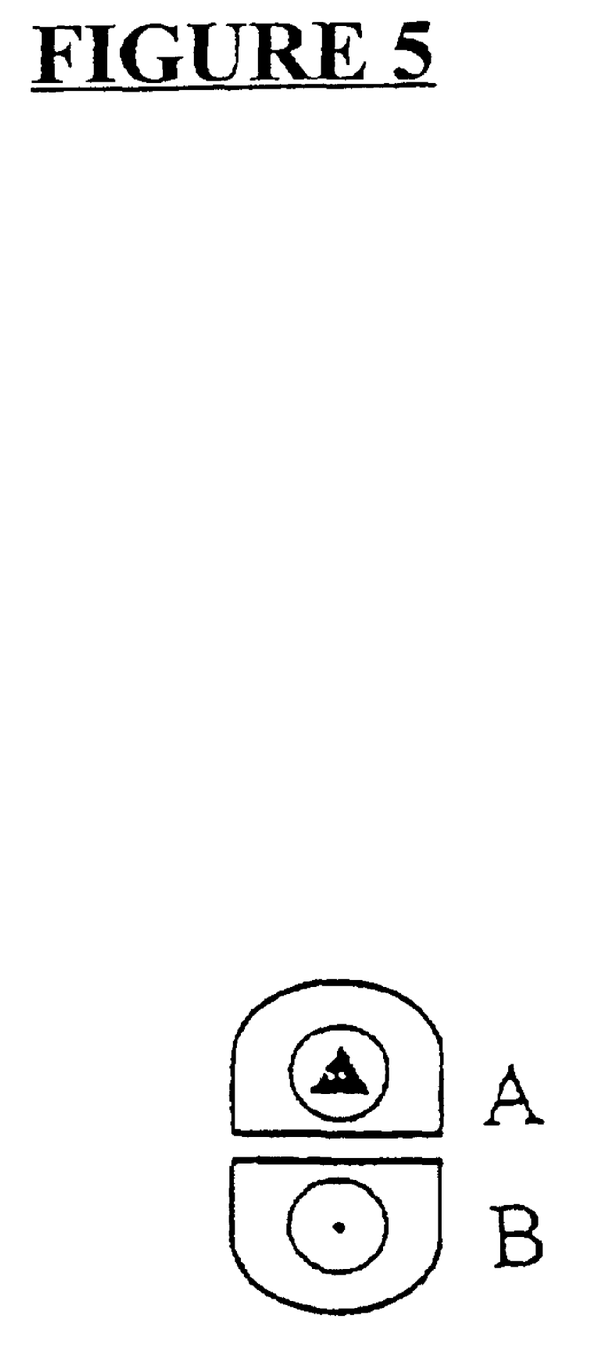
FIG. 5 is a perspective view of the preferred assay device illustrating a positive test for Influenza A.
Figure 6:
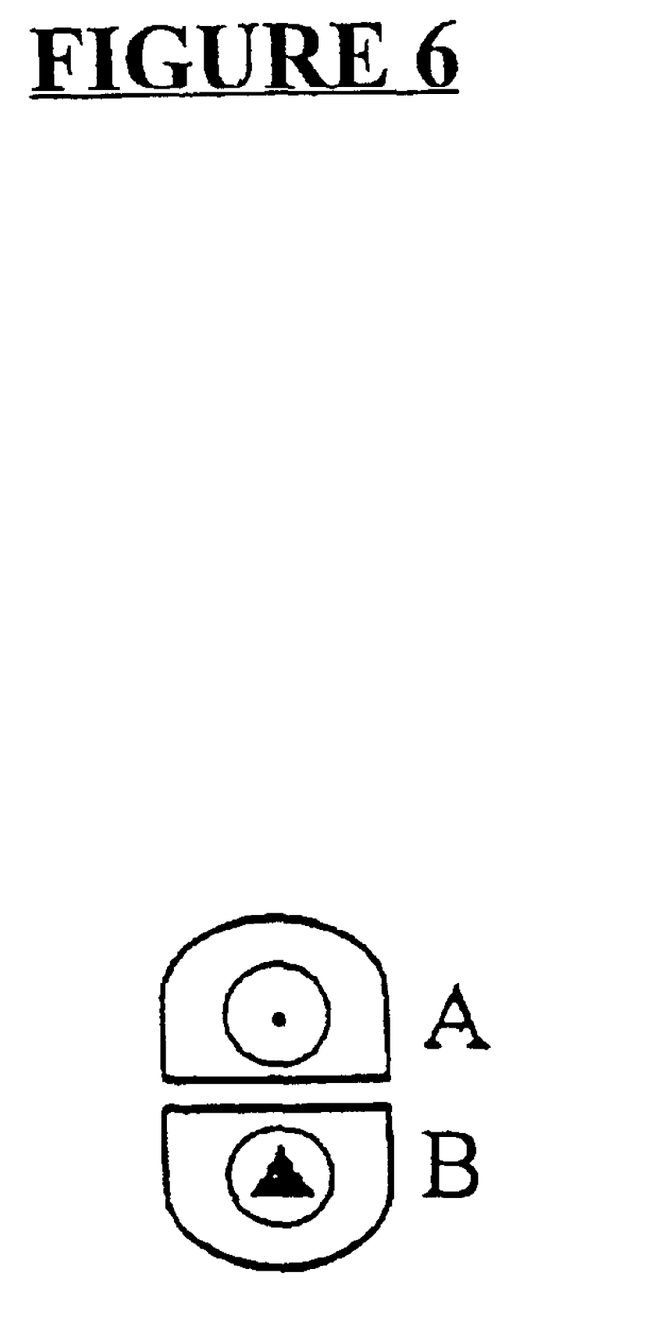
FIG. 6 is a perspective view of the preferred assay device illustrating a positive test for Influenza B.

Referring now to FIG. 5, there is illustrated a positive test for Influenza A. As seen therein, a triangle of any intensity appears on the membrane in the A well and indicates Influenza A antigen is present and detectable in the specimen. The background area surrounding the triangle will preferably be a light yellow to light purple color. A control dot should also be evident in the center of the triangle unless obscured by an intense positive reaction. FIG. 6 is identical to FIG. 5, except that FIG. 6 illustrates a positive test for Influenza B.

Figure 7:
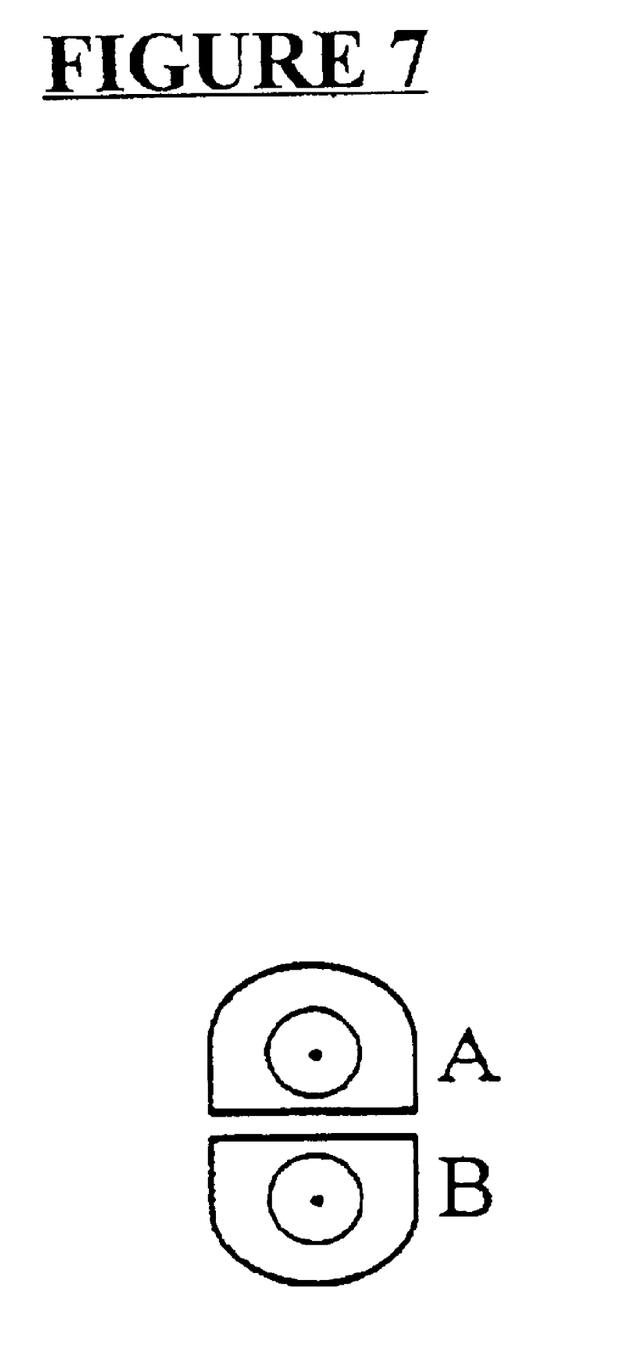
FIG. 7 is a perspective view of the preferred device illustrating a negative test for both Influenza A and Influenza B.

Referring now to FIG. 7, there is illustrated a negative test for Influenza A and Influenza B. As seen therein, no triangle is visible in either the A well or the B well, indicating that neither influenza antigen is present and detectable in the specimen. The appearance of a control dot on the membrane in each of the wells indicates proper performance of test procedures and reagents.

If desired, control reagents may be used in place of patient samples for quality control purposes. The control reagents may be used as a means of additional quality control (i.e., in addition to the internal positive and negative procedural controls) to demonstrate a positive or negative reaction. The same method as previously described is used except that control A+/B− or control B+/A−, rather than a patient specimen, is mixed with the extraction reagent. Control A+/B− serves as a positive control for Influenza A, as well as a negative control for Influenza B, while control B+/A− serves as a positive control for Influenza B and a negative control for Influenza A. The formation of, for example, a purple triangle, on the membrane in the A well of the device when control A +/B− is tested and on the membrane in the B well of the device when control B+/A− is employed further indicates that the antigen binding properties of the membrane are functional. The formation of only, for example, a purple control dot, in the B well of the device when control A+/B− is employed is an appropriate Influenza B negative control result that indicates proper reagent function and assures that the correct test procedure has been followed. Similarly, the formation of only, for example, a purple control dot, in the A well of the device when control B+/A− is employed is an appropriate Influenza A negative control result.

The control reagents may also be used to demonstrate a low positive reaction. Such a weaker positive reaction may be demonstrated by dilution of both control reagents together.

The device and method of the present invention may also be used to differentiate the presence of respiratory syncytial virus ("RSV") from influenza in a single patient sample.

The device and method of the present invention may also be used to detect more than one analyte in one or more of the wells of the test device. Two or more analytes may be detected in a single well by development of both analytes in a single visual character formed on the membrane of the test device, by development of two or more characters in a single well of the test device or by development of two or more colors in a single well of the test device.

As a matter of convenience, the test device of the present invention may be provided in a kit, packaged in combination with predetermined amounts of various reagents for use in assaying for one or more analytes. The reagents may include, for example, extraction reagents, wash reagents, detection reagents, substrate reagents and stop reagents. In addition, other additives may be included such as, for example, stabilizers, buffers and the like.

In a preferred embodiment, the reagents of the kit include an extraction reagent, at least one wash reagent, first and second detection reagents and a substrate reagent. The extraction reagent preferably comprises about 1.6% mucolytic agent and about 7.4% detergents with about 0.2% sodium azide (preservative). A first wash reagent comprises about 50 mM Tris and rabbit IgG with about 0.2% sodium azide. Additional wash reagents may also be included. Preferably, a second wash reagent comprises about 5% butanol, about 2 M urea and about 100 mM Hepes with about 0.2% sodium azide, while a third reagent comprises about 50 mM Tris and about 150 mM NaCl with about 0.2% sodium azide. The first detection reagent preferably comprises anti-Influenza A monoclonal murine antibodies (2)-enzyme conjugate with about 0.2% sodium azide. The second detection reagent preferably comprises anti-Influenza B monoclonal murine antibody-enzyme conjugate with about 0.2% sodium azide. The substrate reagent preferably comprises about 0.73 mM chromogen. The kit may further include a stop reagent, which may be, for example, about 150 mM citric acid.

Two control reagents may also be included in the kit. The first control reagent preferably comprises Influenza A antigen with about 0.1% sodium azide such that it is positive for Influenza A and negative for Influenza B. The second control reagent, which is positive for Influenza B and negative for Influenza A, preferably comprises Influenza B antigen with about 0.1% sodium azide.

Other components that may be included in the kit are tubes for specimen extraction and sample delivery into the test device and tips to filter the sample as it is being delivered into the test device. Suitable tubes and tips include those available under the name DispensTube™.

The speed and workflow of the test of the present invention make it applicable as a "STAT" Influenza A and/or Influenza B antigen detection test, providing rapid, relevant information to assist with the diagnosis of influenza. Use of the present invention to differentiate Influenza A from Influenza B can provide the opportunity for greater selectivity of antiviral intervention.

EXAMPLES

Analytical Studies

Analytical Sensitivity

The analytical sensitivity was evaluated using 13 influenza strains (7 Influenza A strains and 6 Influenza B strains). Serial dilutions prepared using qualified media were tested in triplicate according to the above-described method of the present invention. Viral detection limits were calculated by logistic regression analysis based on viral concentrations and interpretation on test results.

| Influenza Viral Strain | Viral Type | Detection Limit ($CEID_{50}$/mL) |
|---|---|---|
| A/PR/8/34 (H1N1) | A | $8.2 \times 10^3$ |
| A1/FM/1/47 (H1N1) | A | $5.9 \times 10^2$ |
| A/NWS/33 (H1N1) | A | $1.6 \times 10^2$ |
| A1/Denver/1/57 (H1N1) | A | $6.5 \times 10^1$ |
| A/Port Chalmers/1/73 (H3N2) | A | $2.9 \times 10^2$ |
| A/Victoria/3/73 (H3N2) | A | $3.3 \times 10^4$ |
| A/New Jersey/8/76 (H1N1) | A | $2.1 \times 10^2$ |
| B/Lee/40 | B | $1.2 \times 10^6$ |
| B/Allen/45 | B | $1.8 \times 10^2$ |
| B/Maryland/1/59 | B | $4.6 \times 10^1$ |
| B/GL/1739/54 | B | $2.5 \times 10^3$ |
| B/Taiwan/2/62 | B | $6.6 \times 10^2$ |
| B/Hong Kong/5/72 | B | $2.3 \times 10^3$ |

Analytical Specificity and Cross-reactivity

The test device of the present invention was evaluated using 90 microorganisms (58 bacteria, 2 yeast and 30 viruses). Bacteria and yeast isolates were tested at concentrations of about $10^7$ to $10^8$ CFU/mL. A concentration of >$10^8$ CCU/mL was used for *M. pneumoniae*. Viral isolates were tested at titers of about $10^4$ to $10^{10}$ TCID$_{50}$/mL. Influenza C was tested at a titer of about $1.6 \times 10^{10}$ CEID$_{50}$/mL. None of the microorganisms or viruses listed below gave a positive result in the Influenza A and B test device of the present invention.

panel of 62 influenza strains. All of the Influenza A strains gave positive results for Influenza A and negative results for Influenza B. All of the Influenza B strains gave positive results for Influenza B and negative results for Influenza A. All known Influenza A hemagglutinin and neuraminidase subtypes are represented below.

| Microorganism Panel | | |
|---|---|---|
| *Acinetobacter baumannii* | *Kingella kingae* | *Prevotella oralis* |
| *Actinobacillus suis* | *Klebsiella pneumoniae* | *Proteus mirabilis* |
| *Bacteroides fragilis* | *Lactobacillus casei* | *Proteus vulgaris* |
| *Bordetella pertussis* | *Lactobacillus fermentum* | *Pseudomonas aeruginosa* |
| *Candida albicans* | *Lactobacillus plantarum* | *Salmonella choleraesuis* sub *minnesota* |
| *Candida glabrata* | *Legionella pneumophila* | *Serratia marcescens* |
| *Cardiobacterium hominis* | *Listeria monocytogenes* | *Staphylococcus aureus* |
| *Chlamydia psittaci* | *Moraxella catarrhalis* | *Staphylococcus aureus*-Cowen 1 |
| *Chlamydia trachomatis* | *Mycobacterium avium* | *Staphylococcus epidermidis* |
| *Corynebacterium diphtheriae* | *Mycobacterium intracellulare* | *Streptococcus bovis* II Group D |
| *Eikenella corrodens* | *Mycobacterium tuberculosis* | *Streptococcus mutans* |
| *Enterococcus faecalis* | *Mycoplasma orale* | *Streptococcus oralis* |
| *Enterococcus gallinarum* | *Mycoplasma pneumoniae* | *Streptococcus pneumoniae* |
| *Escherichia coli* | *Neisseria gonorrhoeae* | *Streptococcus pyogenes* Group A |
| *Fusobacterium nucleatum* | *Neisseria meningitidis* | *Streptococcus sanguis* |
| *Gardnerella vaginalis* | *Neisseria mucosa* | *Streptococcus* sp. Group B |
| *Haemophilus aphrophilus* | *Neisseria sicca* | *Streptococcus* sp. Group C |
| *Haemophilus influenzae* | *Neisseria subflava* | *Streptococcus* sp. Group F |
| *Haemophilus parainfluenzae* | *Peptostreptococcus anaerobius* | *Streptococcus* sp. Group G |
| *Haemophilus paraphrophilis* | *Porphyromonas asaccharolyticus* | *Veillonella parvula* |

| Viral Panel | |
|---|---|
| Adenovirus Type 3 | HSV Type 2 |
| Adenovirus Type 5 | Influenza C/Taylor/1233/47 |
| Adenovirus Type 7 | Measles virus Edmonston |
| Adenovirus Type 18 | Mumps virus |
| Coronavirus | Parainfluenza Type 1 |
| Coxsackie Type A9 (Griggs) | Parainfluenza Type 2 |
| Coxsackie Type B5 | Parainfluenza Type 3 |
| Coxsackie Type B6 | Rhinovirus Type 1A |
| Coxsackie Type A21 (Kuykendall) | Rhinovirus Type 3 |
| Coxsackie Type A9 (Bosek) | Rhinovirus Type 13 |
| Cytomegalovirus AD-169 | Rhinovirus Type 16 (1-CV15) |
| Echovirus Type 11 | Rhinovirus Type 37 |
| Echovirus Type 3 | RSV A |
| Echovirus Type 6 | RSV B |
| HSV Type 1 | VZV |

Interfering Substances

The following substances were tested in the device of the present invention, and no interference was noted in the assay for any of the substances at the levels tested: whole blood (2%), 4 nasal sprays (25%), acetylsalicylic acid (20 mg/mL), 3 mouthwashes (25%), ibuprofen (10 mg/mL), oseltamivir (0.5 mg/mL), zanamivir (1 mg/mL), chlorpheniramine maleate (5 mg/mL), 4 throat drops (25%), guaifenesin (20 mg/mL), diphenhydramine hydrochloride (5 mg/mL), dextromethorphan hydrobromide (10 mg/mL), pseudoephedrine hydrochloride (20 mg/mL), acetominophen (216 mg/mL), clemastine fumarate (0.35 mg/mL) and phenylpropanolamine hydrochloride (20 mg/mL).

Reactivity and Specificity of Influenza A and Influenza B Strains

The test device and method of the present invention were evaluated to demonstrate reactivity with both human and non-human strains of Influenza A and Influenza B using a

| Influenza Virus Human Isolate | |
|---|---|
| A/PR/8/34 | A/Human/Hong Kong/481/97 |
| A1/FM/1/47 | A/Human/Hong Kong/482/97 |
| A/NWS/33 | A/Human/Hong Kong/228156/97 |
| A1/Denver/1/57 | A/Human/Hong Kong/229540/97 |
| A/New Jersey/8/76 (Hsw N1) | A/Human/Hong Kong/242095/97 |
| A/Hong Kong/9821/2000 | A/Human/Hong Kong/1073/99 |
| A/Hong Kong/2997/98 | A/Human/Hong Kong/1074/97 |
| A/Hong Kong/5405/2000 | B/Lee/40 |
| A/Hong Kong/6611/2000 | B/Allen/45 |
| A/Hong Kong/15946/2000 | B/GL/1739/54 |
| A/Hong Kong/16051/2000 | B/Taiwan/2/62 |
| A/Port Chalmers/1/73 | B/Maryland/1/59 |
| A/Victoria/3/73 | B/Hong Kong/5/72 |
| A/Hong Kong/114313/2000 | B/Hong Kong/28637/2000 |
| A/Hong Kong/117393/2000 | B/Hong Kong/27254/2000 |
| A/Hong Kong/114591/2000 | B/Hong Kong/28636/2000 |
| A/Hong Kong/119563/2000 | B/Hong Kong/29130/2000 |
| A/Hong Kong/120277/2000 | B/Hong Kong/29276/2000 |
| A/Hong Kong/68012/2000 | B/Hong Kong/35952/2000 |

| Influenza Virus Animal Isolate | |
|---|---|
| A/Turkey/Kansas/4880/80 | A/Turkey/Ontario/6118/67 |
| A/Asia/57 | A/Chicken/Hong Kong/G9/97 |
| A/Mallard/New York/6750/78 | A/Swine/Hong Kong/9/98 |
| A/Swine/Hong Kong/5212/99 | A/Turkey/Wisconsin/66 |
| A/Turkey/England/69 | A/Quail/Hong Kong/G1/97 |
| A/Duck/Hong Kong/477/78 | A/Duck/Hong Kong/865/80 |
| A/Chicken/Alabama/75 | A/Chicken/Germany/N/49 |
| A/Turkey/Wisconsin/68 | A/Duck/Memphis/546/74 |
| A/Goose/Hong Kong/38/79 | A/Duck/Alberta/60/76 |
| A/Turkey/Canada/63 | A/Gull/MD/704/77 |
| A/Turkey/Oregon/71 | A/Mallard/Gurjev/263/82 |
| A/Duck/Hong Kong/47/76 | A/Shearwater/WA/2576/79 |

Having now fully described the invention with reference to certain representative embodiments and details, it will be apparent to one of ordinary skill in the art that changes and modifications can be made thereto without departing from the spirit or scope of the invention as set forth herein.

What is claimed is:

1. A kit for performing a flow-through analytical test for detecting the presence of and distinguishing between Influenza A viral antigens and Influenza B viral antigens in a biological sample suspected of containing one or both of Influenza A viral antigens and Influenza B viral antigens, the kit comprising:
- (a) an analytical test device having a plurality of wells, wherein the wells do not communicate with each other; and wherein each well comprises:
  a filter stack, the filter stack comprising:
  - (i) a porous membrane having an upper surface and a lower surface; and
  - (ii) an absorbent material, wherein said lower surface of said porous membrane and said absorbent material are in physical contact and in fluid communication, and wherein upon contact of a biological fluid sample suspected of containing one or both of the Influenza A viral antigens and the Influenza B viral antigens with said porous membrane, said fluid is able to flow through said membrane into said absorbent material, such that at least a portion of said viral antigens present in said biological fluid sample bind to said porous membrane;
- (b) a first detection reagent capable of recognizing Influenza A viral antigens;
- (c) a second detection reagent capable of recognizing Influenza B viral antigens; and
- (d) a reagent capable of generating a signal upon detection of one or both of Influenza A viral antigens and Influenza B viral antigens.

2. The kit of claim 1, wherein the test device comprises two wells.

3. The kit of claim 1, wherein the first detection reagent comprises an anti-Influenza A monoclonal murine [antibodies (2)] antibody-enzyme conjugate.

4. The kit of claim 1, wherein the second detection reagent comprises an anti-Influenza B monoclonal murine antibody-enzyme conjugate.

5. The kit of claim 1, wherein the reagent capable of generating a signal comprises chromogen.

6. The kit of claim 1, further comprising an extraction reagent.

7. The kit of claim 6, wherein the extraction reagent comprises a mucolytic agent.

8. The kit of claim 1, further comprising at least one wash reagent.

9. The kit of claim 1, further comprising a stop reagent.

10. The kit of claim 9, wherein the stop reagent comprises citric acid.

* * * * *